United States Patent [19]

Allen

[11] Patent Number: 5,651,970
[45] Date of Patent: Jul. 29, 1997

[54] METHOD FOR INHIBITING DISEASE ASSOCIATED WITH THE HUMAN IMMUNODEFICIENCY VIRUS THROUGH THE USE OF MONOCLONAL ANTIBODIES DIRECTED AGAINST ANTI-SELF CYTOTOXIC T-LYMPHOCYTES OR THEIR LYTICS

[76] Inventor: Allen D. Allen, 4236 Longridge Ave., Penthouse 302, Studio City, Calif. 91604

[21] Appl. No.: 483,745

[22] Filed: Jun. 7, 1995

Related U.S. Application Data

[63] Continuation-in-part of Ser. No. 302,113, Sep. 7, 1994, Pat. No. 5,424,066, which is a continuation of Ser. No. 165,751, Dec. 13, 1993, abandoned, which is a continuation-in-part of Ser. No. 33,405, Mar. 19, 1993, abandoned.

[51] Int. Cl.$^6$ .................... A61K 39/395; C07K 16/28
[52] U.S. Cl. .................... 424/154.1; 424/130.1; 424/156.1; 530/388.2; 530/388.75; 530/388.85
[58] Field of Search ................ 424/154.1, 130.1, 424/156.1; 530/388.2, 388.75, 388.85

[56] References Cited

U.S. PATENT DOCUMENTS 5,002,869  3/1991  Schlossman et al. .

OTHER PUBLICATIONS

Zarling et al., J. Immunol., 144(8): 2992, 1990.
Butini et al., Eur. J. Immunol., 1994, 24:2191.
*Immune–Based Therapeutics: Scientific Rationale and the Promising Approaches to the Treatment of the Human Immunodeficiency Virus–Infected Individual*, Stein et al., CID 1993:17 (October).
*Immunoreconstitution of T–Cell Impairments in Asymtomatic Male Homosexuals by Thymic Hymoral Factor (THF)*, Handzel, et al., Int. J. Immunopharmac., vol. 9, No. 2, pp. 165–173, 1987.
*Prospects of AIDS Therapy by Thymic Humoral Factor, a Thymic Hormone*, Nathan Trainin, Nat Immun Cell Growth Regul 1990; 9:155–159.
*Research Review, Functional anatomy of the thymic microenvironment*, Marion D. Kendall, J. Anat. (1991), 177, pp. 1–29.

*Primary Examiner*—Christina Y. Chan
*Assistant Examiner*—Frank C. Eisenschenk
*Attorney, Agent, or Firm*—David H. Judson

[57] ABSTRACT

Methods for treating and inhibiting disease and symptoms associated with the human immunodeficiency virus (HIV) are provided. The method includes transforming the human immunodeficiency virus (HIV) infection into a nonserious disease through the infusion of monoclonal antibodies directed against particular antigens on anti-self, anti-CD4 cytotoxic T-lymphocytes.

1 Claim, 2 Drawing Sheets

METHOD FOR INHIBITING DISEASE ASSOCIATED WITH THE HUMAN IMMUNODEFICIENCY VIRUS THROUGH THE USE OF MONOCLONAL ANTIBODIES DIRECTED AGAINST ANTI-SELF CYTOTOXIC T-LYMPHOCYTES OR THEIR LYTICS

CROSS REFERENCE TO RELATED APPLICATION

This application is a continuation-in-part of application U.S. Ser. No. 08/302,113, filed Sep. 7, 1994, now U.S. Pat. No. 5,424,066 which is a file wrapper continuation of U.S. Ser. No. 08/165,751, filed Dec. 13, 1993, now abandoned, which application is a continuation-in-part application of prior application U.S. Ser. No. 08/033,405, filed Mar. 19, 1993, now abandoned.

TECHNICAL FIELD

The present invention relates generally to methods for treating human disease conditions associated with the human immunodeficiency virus (HIV) and more particularly to the use of monoclonal antibodies directed against anti-self cytotoxic T-lymphocytes or their lytics in order to inhibit or treat HIV and related HIV diseases.

BACKGROUND OF THE INVENTION

Several viruses produce latent infection in humans and can reactivate to produce recrudescent or persistent disease. One such disease is the human immunodeficiency virus (HIV). HIV is associated with a progressive catastrophic disease in certain primates, including humans. Humans infected with HIV experience proliferation of a certain class of white blood cells known as cytotoxic T-lymphocytes (CTL). The final stage of this disease is commonly known as acquired immune deficiency syndrome (AIDS).

It is well known in the art that the clinical signs and symptoms of AIDS are primarily due to a profound loss of all lymphocytes marked with the CD3 and CD4 antigens (CD4+ T-lymphocytes). It is also generally accepted that the infectious agent in AIDS is the human immunodeficiency virus (HIV). Although HIV infects and destroys CD4+ cells, the number of cells infected is inadequate to account for the profound and indiscriminate loss of these cells that occurs in individuals infected with HIV. It has been suggested by those in the field that autoimmunity may play a role in the pathogenesis of AIDS. However, few have suspected a pathogenic cytotoxic T-lymphocyte (CTL).

Rather, it is generally accepted by those skilled in the art that CTL's are beneficial for those infected with HIV since it is believed CTL's help control the infection, i.e., CTL's are believed to be prognosticators that delay the progression of AIDS. Kilmas, et at, "Phase I Trial of Adoptive Therapy with Purified CD8 Cells in HIV Infection", Int. Conf. AIDS, Jul. 19–24, 1992; Abstract No. POB 3446, for example, have described infusion of CTL's into the bloodstream of HIV-infected patients as an experimental method of treatment. This particular type of infusion was directed to the mitogen-expanded colonies of the host patient's autologous CD8+ cells, a lymphocyte population that includes CTL's.

However, Zarling, et at, "HIV-Infected Humans, But Not Chimpanzees, Have Circulating Cytotoxic T-Lymphocytes That Lyse Uninfected CD4+ Cells", *J. Immunol.,* 1990; 144: 2992–98 have shown that HIV-infected humans have an anti-self, anti-CD4 CTL in their circulating blood that lyses healthy, uninfected CD4+ cells. No such CTL was found in the blood of HIV-seronegative humans. Moreover, no such CTL or suicide cell was found in the blood of HIV-infected chimpanzees. This is significant because HIV infection manifests as a nonpathogenic colonization in the blood and tissue of chimpanzees.

BRIEF SUMMARY OF THE INVENTION

HIV vaccine studies have shown that reducing CTL's causes the host's CD4 count to go up. The present invention is based on the deduction that the reason CD4 counts go down in the first place as a result of HIV infection is because among the various types of CTL's, there must be an anti-self, anti-CD4 CTL. Thus, the maladaptive CTL synthesized by humans is the factor that transforms HIV infection into a catastrophic disease. This is confirmed by the work of Zarling et al, who found that because HIV infection does not lead to any serious disease in chimpanzees, it is the anti-self, anti-CD4 suicide cell, rather than HIV itself, that is directly responsible for the disease associated with HIV infection in humans.

The destructive role of the anti-self, anti-CD4 cytotoxic T-lymphocyte is overcome according to the teachings of the present invention through the use of monoclonal antibodies directed against one or more particular antigens on the anti-self, anti-CD4 killer cell or antigens on the lytics produced by such killer cell. Through infusion of particular monoclonal antibodies directed against such antigens, the anti-self, anti-CD4 cytotoxic T-lymphocytes or their lytics as the case may be are neutralized to prevent an HIV positive patient from developing AIDS or to cure the disease itself if the disease has sufficiently advanced into AIDS. In addition, use of adhesion antibodies neutralizes cells producing HIV to improve the health of infected patients.

It is thus a primary objective of the present invention to provide a method for preventing and/or curing HIV disease by eliminating or neutralizing anti-self, anti-CD4 CTL's or their lytics from the circulating blood of an HIV-infected patient through the infusion of monoclonal antibodies directed against the antigens presented by such cells or their lytics.

These and other objects of the invention are provided in a method which transforms HIV into a nonserious infection. This is accomplished by neutralizing or removing the anti-self, anti-CD4 suicide cell from the circulating blood of an individual infected with HIV or who is at risk of such infection, and by neutralizing or removing HIV-producing cells.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which.

DETAILED DESCRIPTION

By way of brief background, it is well known that cytotoxic T-lymphocytes ("CTL's") are white blood cells that kill other cells. If a CTL kills foreign cells (such as bacteria, fungus, viruses, cancer or the like), it is deemed a normal cytotoxic T-lymphocyte. On the other hand, if the CTL kills healthy cells of the body that the cell belongs to, it is deemed an "anti-self" cytotoxic T-lymphocyte. In either case, such cells typically function by destroying the cell membrane of the target cell using one or more "lytics", which are known chemical compounds. The process of breaking apart the target cell is referred to as lysis.

CTL's belong to a group of lymphocytes that carry a CD8 antigen. HIV vaccine studies have shown that reducing CTL's causes a host patient's CD4 count to go up. From this evidence, it has now been recognized that the reason CD4 counts go down in the first place as a result of HIV infection is because among the CTL's, there must be an anti-self, anti-CD4 CTL. Thus, AIDS is caused not by the infection itself, but by a white blood cell made in response to the infection.

Figure 1:
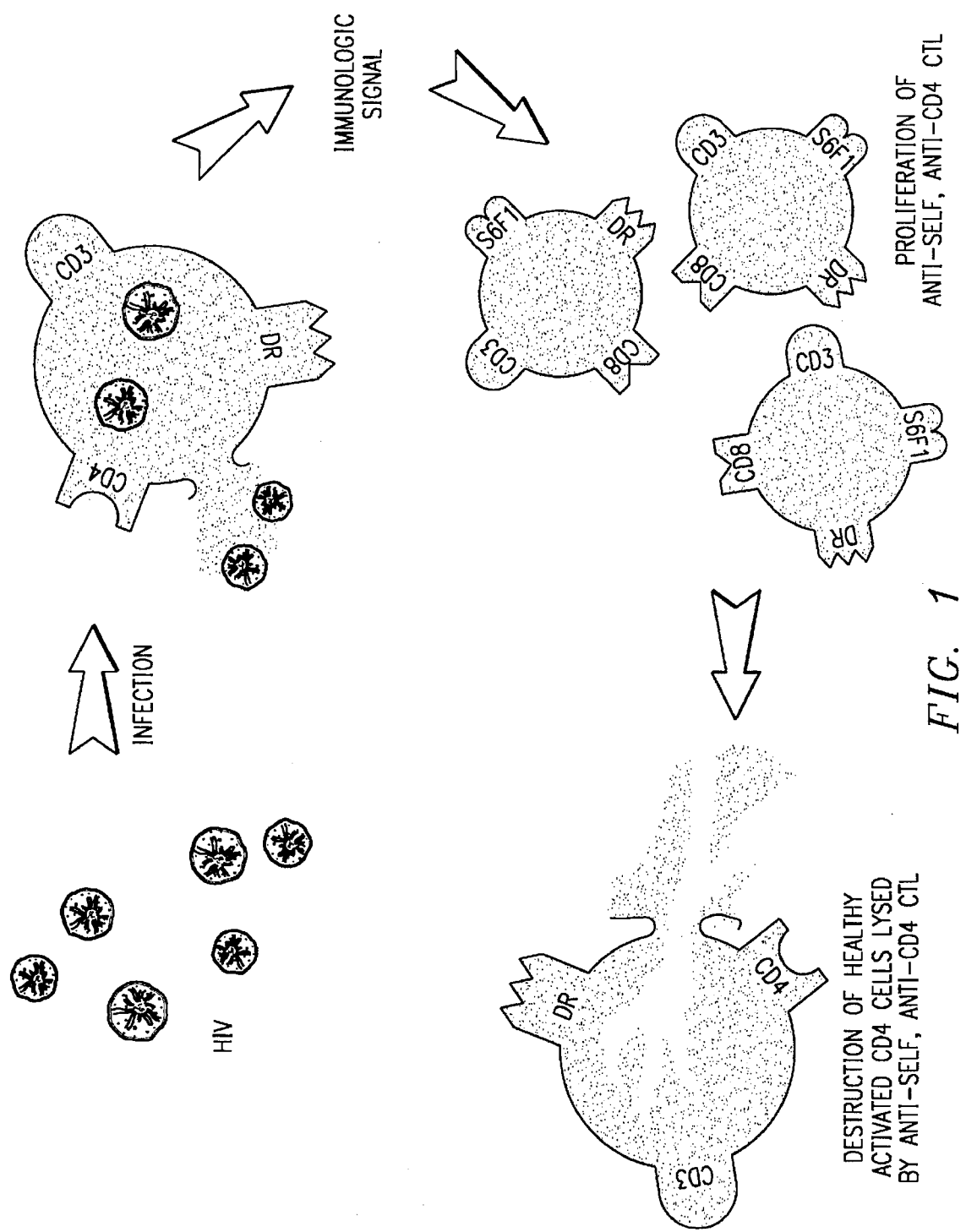
FIG. 1 is a schematic representation of AIDS pathogenesis showing the role of the anti-self, anti-CD4 CTL in the progression of HIV disease into AIDS.

FIG. 1 is a schematic representation of what is believed to be the AIDS pathogenesis. As seen in this figure, the HIV infection leads to the destruction of CD4 cells through infection and budding of new HIV virions. This process generates an immunologic signal that causes the proliferation of anti-self, anti-CD4 cytotoxic T-lymphocytes. As shown in FIG. 1, these cells carry various known antigens including, without limitation, DR, CD8, LFA-1, ICAM and TCR-1. The cells also include one or more lytics which are chemical compounds used to attack the target cell; such lytics also include antigens. The anti-self, anti-CD4 CTL's or their lytics then destroy healthy activated CD4 cells. Thus AIDS is probably caused not by the infection itself but by the white blood cells made in response to the infection.

The present invention overcomes the destructive action of the anti-self, anti-CD4 CTL's or their lytics by infusion of monoclonal antibodies into the bloodstream of the host patient. It also overcomes the deleterious effects of HIV replication. As is known in the art, a monoclonal antibody is an antibody that is made from one cell so that all resulting antibodies are the same. The standard process of making monoclonal antibodies is described in, for example, Immunology III, by Joseph A. Bellanti (W. B. Sanders, 1985) at pages 99-100, which teachings are incorporated herein by reference. Of course, the particular method for making the monoclonal antibodies is not limited to such technique and it is envisioned that any technique for making such antibodies is within the practice of the invention. The antibodies are designed to be directed toward a particular antigen on the anti-self, anti-CD4 CTL or an antigen on lytics produced by such CTL.

Figure 2:
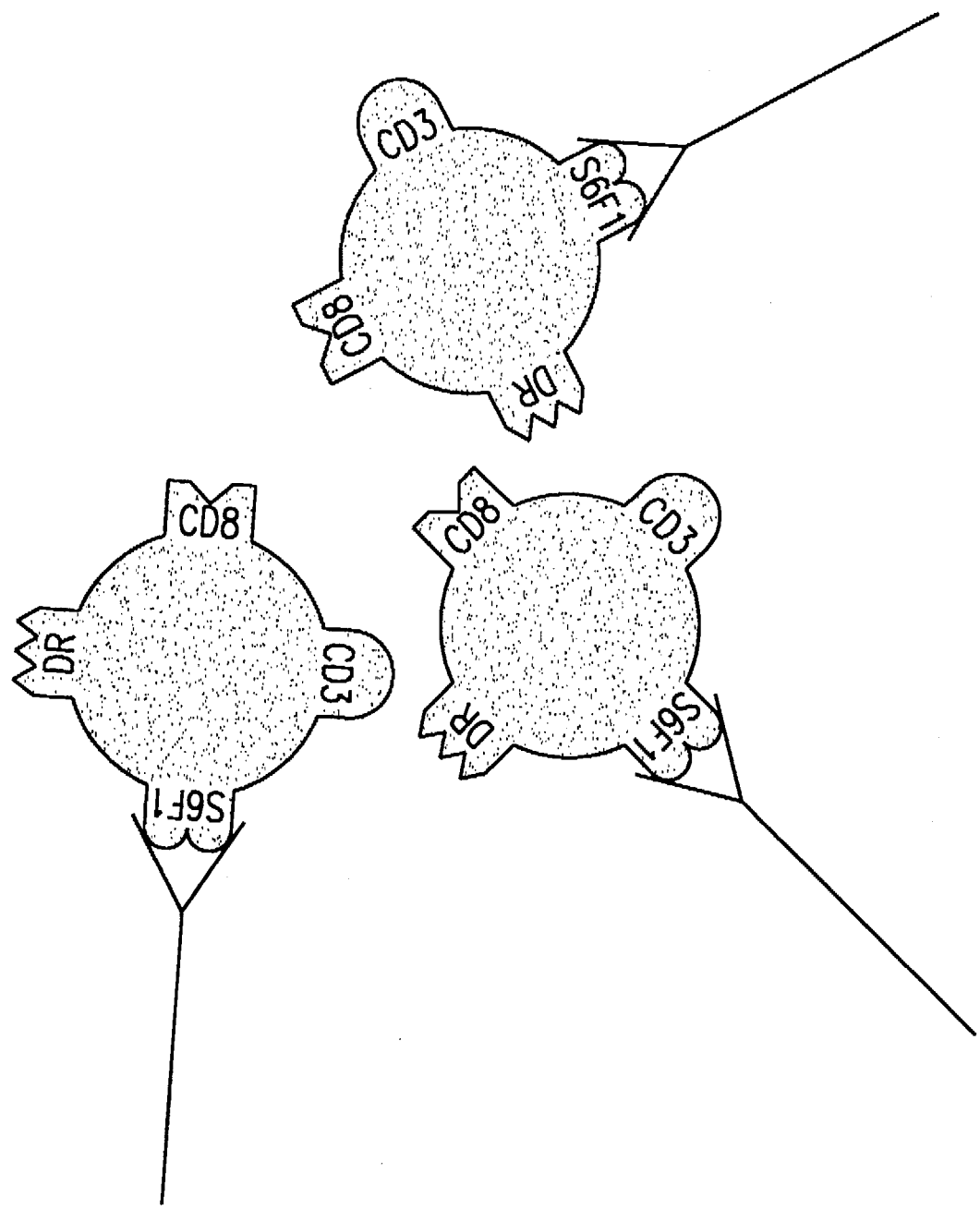
FIG. 2 is a schematic representation of a S6F1 monoclonal antibody attached to the S6F1 antigen on the anti-self CTL according to the teachings of the present invention.

Referring now to FIG. 2, a representation is shown of the particular treatment method. As seen, monoclonal antibodies directed against a specific antigen, in this case the S6F1 antigen on the anti-self, anti-CD4 CTL, are produced in the conventional manner and infused into the bloodstream of the host patient. The particular monoclonal antibody is shown attached to the antigen. Such mating flags the immune system and triggers a known immunological response to cause the body to attempt to neutralize the cells. In this manner, the anti-self, anti-CD4 CTL cell is neutralized. A similar mechanism would be used if the particular monoclonal antibodies were directed to an antigen on a lyric produced by the CTL cell.

According to the invention, monoclonal antibodies are directed to one or more of the antigens on the CTL cell or its lytics. Under some circumstances, it may be desirable to limit the type of monoclonal antibodies to certain specific antigens. Or, it may be desirable to treat the patient first with a particular monoclonal antibody and then use another monoclonal antibody later, or to use multiple antibodies simultaneously. Thus, for example, since many cells (besides the CTL) carry the CD8 antigen, it may be desirable to limit use of the CD8 monoclonal antibodies until an initial improvement in the patient's immune system is established through some other antigen target. The present invention is intended to cover all such variations on the sequence and scope of how the particular monoclonal antibodies are infused.

Although not meant to be limiting, the monoclonal antibodies are preferably infused once per month over a period of between 10 minutes in accordance with one embodiment of the invention. The mount of antibodies should typically be about 0.1 milligrams per kilogram of the patient's body weight. The daily regimen is preferably repeated as needed to maintain an effective immune response. As used herein, an effective immune response will typically mean that the patient's CD4/CD8 ratio is returning to normal, accepted levels. While different laboratories have different norms, usually this will mean a ratio of about 1:1. Thereafter, maintenance treatments may be required depending on the course of the infection or disease. Preferably, the patient's blood should be measured on a monthly basis to track the progress of the treatment. Although not meant to be limiting, the monoclonal antibodies are typically supported in a suitable carrier such as PBS Ringer's lactate solution or normal saline. The infusion may be effected using a conventional syringe and line or infusion pump of known manufacture.

As discussed above, the present invention thus exploits the belief that it is the immunogenic component of the HIV infection that results in the progression of HIV to a fatal disease. The significance of the present invention is that it provides a method of neutralizing the maladaptive CTL (or its lytics) that transform HIV infection into AIDS. Thus according to the invention the HIV disease can be transformed from a non-serious infection, and HIV infection can be prevented from becoming a serious disease, if the suicide cell and/or its lytics are neutralized in, or removed from, an individual infected with HIV or at risk of such infection.

Thus the method transforms HIV infection through the infusion of monoclonal antibodies directed against anti-self CTL's or their lytics. This approach recognizes that monoclonal antibodies have a direct and specific effect against the body of specific antigens. According to the invention, a necessary but sufficient dose of monoclonal antibodies is infused into the bloodstream until anti-self CTL's have been eliminated or neutralized and HIV disease cured, or anti-self CTL's are incapable of proliferating and HIV disease has thereby been prevented.

EXPERIMENTAL

A patient, infected with the HIV virus for about ten years, had been receiving treatment by injection of his own T cells to achieve a biphasic elevation of the CD4/CD8 ratio. The patient had been responding to such injections for a period of about fifteen months of treatment. At that time, the patient had also been on ddI for approximately two years. However, given the advanced stage of the patients' disease, both of these treatments were no longer providing beneficial results. In fact, HIV could be cultured from his blood cells even when the blood was diluted out to about one part per 3,120. Even at such dilution, the p24 antigenemia, which is a measure of HIV activity, was quite high at about 300 pg/ml.

The patient was then treated in accordance with the method of the present invention. In particular, the patient was given about 68 mg of S6F1 antibodies over a period of 14 days. The 68 mg corresponded to 1 mg/kg of the patient's body weight. A few days after completing the treatment, the AIDS virus could no longer be cultured from the circulating blood cells of the patient. Thus, treatment in accordance with the present invention reduces viral load in the circulating blood of patients with long-term HIV infection.

The speed with which infectious cells disappeared from the patient's circulating blood suggests that some phagocyte may have destroyed the infected cells. In fact, the patient experienced a marked increase in monocytes during treatment, and the treating physician believed at the time, that these monocytes could be destroying the infected cells. However, the antiviral effect could also be due to the blockage of the adhesion pathway needed for communication between antigen presenting cells, thus rendering HIV-infected cells noninfectious.

Depending on the progression of disease in the individual and other factors, the dosage range varies from about 0.01 to about 1.0 mg/kg body weight for a patient treated in accordance with the present invention.

The effectiveness of Applicant's method using LFA-1, ICAM-1, ICAM-2 AND ICAM-3 monoclonal antibodies on CD4+ T lymphocyte depletion is illustrated in Butini, et al, "Intercellular adhesion molecules (ICAM)-1, ICAM-2 and ICAM-3 function as counter-receptors for lymphocyte function-associated molecule 1 in human immunodeficiency virus-mediated syncytia formation", *European Journal of Immunology*, 1994, Vol. 24, pp. 2191-2195. The monoclonal antibodies utilized within the experiments discussed in the Butini article included the hybridoma cell lines for TS1/22 and TS1/18 monoclonal antibodies, directed against LFA-1 antigens. RR1/1, CBR-IC2/1 and CBR-IC2/2 monoclonal antibodies were directed against ICAM-1 and ICAM-2 antigens. CBR-IC3/1 and CBR-IC3/2 monoclonal antibodies were directed against two different isotopes of ICAM-3 antigens.

Particularly with respect to CD4+ T lymphocyte depletion, the treatment of cultures with LFA-1 monoclonal antibodies significantly reduced the amount of CD4+ T cell depletion in the treated cultures as compared with the untreated cultures. The CD4+ T cells remain completely viable until day ten after infection and showed only a minor depletion of CD4+ T cells (approximately 20%) at day 19. In untreated cultures, a decrease in CD4+ T cell viability was evident at day 10, and by day 16 the depletion of CD4+ T cells was 80%. Similar results were obtained in cultures treated with ICAM-1, ICAM-2, and ICAM-3 monoclonal antibodies. However, the depletion protection of day 19 was not as high as that achieved with LFA-1 monoclonal antibodies and the depletion was in the 50% range.

An alternative embodiment of the present invention also serves as a preventative measure for health care workers. In particular, an HIV-infected individual requiring invasive medical or dental procedures, undergoes treatment in accordance with the present invention prior to such surgery or procedures. In this manner, infectious cells in the circulating blood of the HIV-infected individual are reduced, thereby protecting health care workers involved with the surgical procedures by reducing the possibility of HIV exposure.

It should be appreciated by those skilled in the art that the specific embodiments disclosed above may be readily utilized as a basis for modifying or designing other techniques or processes for carrying out the same purposes of the present invention. Thus, for example, other delivery vehicles or techniques may be used for delivering the monoclonal antibodies to the bloodstream. It should also be realized by those skilled in the art that such equivalent processes do not depart from the spirit and scope of the invention as set forth in the appended claims.

What is claimed is:

1. A method for treating a patient having suppressed immune function resulting from human immunodeficiency virus infection in order to elevate the number of CD4+ cells in said patient, comprising the steps of:
   (a) infusing a dose of a monoclonal antibody selected from the group consisting of antibodies which specifically bind to ICAM-1, ICAM-2, and ICAM-3, said dose being between about 0.1-1.0 milligrams of said monoclonal antibody per kilogram of the patient's weight; and
   (b) repeating said infusion as necessary.

* * * * *